United States Patent
Fore et al.

(10) Patent No.: US 7,351,058 B2
(45) Date of Patent: Apr. 1, 2008

(54) ARCH BAR

(76) Inventors: Frank Fore, 40 E. Riverside Dr., Jupiter, FL (US) 33469; Michael Cassatly, 8 W. Riverside Dr., Jupiter, FL (US) 33469

( * ) Notice: Subject to any disclaimer, the term of this patent is extended or adjusted under 35 U.S.C. 154(b) by 0 days.

(21) Appl. No.: 11/353,637

(22) Filed: Feb. 14, 2006

(65) Prior Publication Data

US 2007/0190475 A1    Aug. 16, 2007

(51) Int. Cl.
*A61C 3/00* (2006.01)

(52) U.S. Cl. .......................... 433/18; 433/19
(58) Field of Classification Search ............ 433/6, 433/20, 18, 19, 3, 9; 606/69, 70, 71; 602/5, 602/6, 12, 17, 18, 19
See application file for complete search history.

(56) References Cited

U.S. PATENT DOCUMENTS

| | | | | |
|---|---|---|---|---|
| 1,638,006 A | * | 8/1927 | Aderer | 602/5 |
| 1,797,481 A | * | 3/1931 | Preston | 602/5 |
| 2,133,859 A | * | 10/1938 | Hawley | 606/69 |
| 3,474,779 A | * | 10/1969 | Wall, Jr. | 433/18 |
| 3,593,709 A | * | 7/1971 | Halloran | 606/69 |
| 3,955,567 A | * | 5/1976 | Richmond et al. | 606/69 |
| 4,202,328 A | * | 5/1980 | Sukkarie | 433/18 |
| 4,230,104 A | * | 10/1980 | Richter | 433/18 |
| 4,504,229 A | * | 3/1985 | Garito et al. | 433/215 |
| 4,813,869 A | * | 3/1989 | Gatewood | 433/18 |
| 5,184,955 A | | 2/1993 | Baer et al. | |
| 5,842,856 A | * | 12/1998 | Casey | 433/19 |
| 6,086,365 A | * | 7/2000 | Fields | 433/18 |
| 2002/0068254 A1 | | 6/2002 | Campbell | |
| 2003/0044754 A1 | * | 3/2003 | Deslauriers et al. | 433/215 |

FOREIGN PATENT DOCUMENTS

SU    1577790    *    7/1990

* cited by examiner

*Primary Examiner*—Cris Rodriguez
*Assistant Examiner*—Sunil K. Singh
(74) *Attorney, Agent, or Firm*—McHale & Slavin, P.A.

(57) ABSTRACT

An improved arch bar for dental surgery is formed from a strip of malleable material. The strip is the shape of a right angle having a splint portion and a retainer portion. A series of apertures extend through the splint portion and the retainer portion with the longitudinal edges of the strip being continuous and smooth. The splint portion is attached to the bone and the retainer portion forms an outwardly projecting shelf having a smooth surface. The soft tissue of the mouth is protected from ligature wires threaded through the apertures by the shelf.

1 Claim, 2 Drawing Sheets

ARCH BAR

FIELD OF THE INVENTION

This invention relates to oral and maxillofacial surgery using fixation devices to reduce fractures of the facial bones involving the teeth.

BACKGROUND OF THE INVENTION

Conventional practice in reduction or fixation of fractured facial bones involving the teeth and other maxillo-mandibular injuries include placing a splint or arch bar external to the teeth and secured by adhesives or wire to the teeth. An upper bar and a lower bar are connected by wire or flexible elastic bands, as shown by Richter, U.S. Pat. No. 4,230,104. The upper and lower bars have attachment points, called lugs, on the outer surface for the wire or bands. These attachment points cause trauma to the soft tissue on the inside of the mouth and lips. The trauma is a source of discomfort, pain and infection to the patient.

Another conventional way of fixing the upper and lower jaws after corrective maxillomandibular surgery or trauma is by immobilizing either the maxillary or mandibular structures by use of elongated bars which are secured to the buccal and labial faces of the patients teeth. These arch bars are secured by fine circumdental wires that are wrapped around some of the teeth. These arch bars allow for the circumdental wires to be placed only above or below the arch bar itself. The installation of these arch bars takes considerable time during which the patient is typically under a general anesthetic facing the problems therewith.

Other securements include the use of several small brackets which are secured to the patients teeth and then interconnected by a complex set of maxillo-mandibular fixation wires. The interconnecting by wires is complex and presents jagged outer surfaces that can cause discomfort to the patient.

Fields, U.S. Pat. No. 6,086,365, discloses another arch bar with studs on the exterior surface for securing ligature wires. The exposed ligature wire, as well as the studs, can cut or otherwise traumatize the inside of the mouth.

Baer, U.S. Pat. No. 5,184,995 discloses a device for temporary dental splinting employing a wire on which annular composite carriers are arranged. The composite carriers are flexible synthetic material, such as extruded tube which allows plastically deformability by finger pressure.

Gatewood, U.S. Pat. No. 4,813,869 discloses a jaw fixation device employing an anchor member mounted around one or more of the teeth on each jaw which are then strapped together.

Campbell, U.S. Patent Appl. No. 2002/0068254 A1 discloses a jaw anchorage device which employs a flexible belt that extends around and between the teeth. A locking means is a plurality of inclined teeth on both a second section of the belt and an inner face of a locking head whereby the teeth cooperate such that belt can only pass through the aperture in one direction.

What is needed in the art is an arch bar with attachment points for ligature wire that presents a smooth outer surface reducing trauma to the tissue of the mouth. Also needed is an arch bar that allows for the circumdental wires to pass "through" the arch bar as well as above or below the arch bar.

SUMMARY OF THE INVENTION

Disclosed is an apparatus for use in reducing and fixing fractures in the jaw. The apparatus includes an upper arch bar and a lower arch bar, each arch bar adapted to be formed into an arcuate shape having a convex side and a concave side. The upper arch bar and the lower arch bar each have a splint portion and a retainer portion. The retainer portion disposed approximately normal to the splint portion on the convex side. Each splint portion includes a bone engaging surface on the concave side and a series of apertures through each splint portion and each retainer portion. Each splint portion and each retainer portion terminating in a smooth continuous surface for engaging the inside of the mouth.

Therefore, it is an objective of this invention to provide an improved arch bar designed to reduce irritation and trauma to the soft tissue on the inside of the mouth and lips.

Another objective of this invention is to provide an improved arch bar with a smooth uniform exterior surface to engage the inside of the mouth.

A further objective of this invention is to provide an improved arch bar with a shelf containing enclosed attachments lots for ligature wire thereby separating the ligature from the tissue of the mouth.

An additional objective is to allow the circumdental wires to pass through the arch bar windows, as well as above and below the arch bar, decreasing installation time and thus operating room time and the associated risk to the patient by decreasing general anesthesia.

Other objectives and advantages of this invention will become apparent from the following description taken in conjunction with the accompanying drawings wherein are set forth, by way of illustration and example, certain embodiments of this invention. The drawings constitute a part of this specification and include exemplary embodiments of the present invention and illustrate various objects and features thereof.

DETAILED DESCRIPTION OF THE INVENTION

Figure 1:
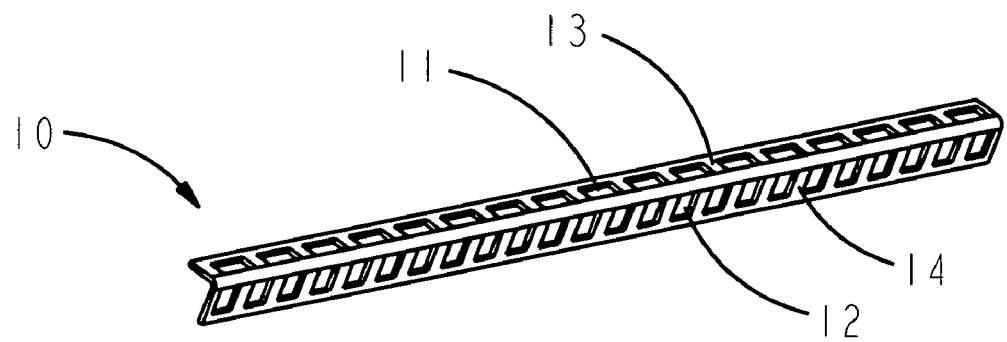
FIG. 1 is a perspective of the arch bar of this invention before application.

The arch bar 10, shown in the drawings, is made from a biologically inert material that is malleable into an arcuate shape, such as metals, coated or un-coated with polymers or ceramics; or plastic compositions of sufficient strength to retain the shaped form in the body to prevent relative movement of broken bones or bone fragments. The arch bar has a series of apertures 11 and 12 formed in two rows along the length of the bar. The apertures 11 are separated by partitions 13 and the apertures 12 (pass through windows) are separated by posts 14. The arch bar 10 may be produced and packages as a straight bar, as shown in FIG. 1 or it may be preformed into a large diameter arc. The surgeon will manipulate the bar to its final dimensions as determined by the physiology and injury of the individual patient.

Figure 2:
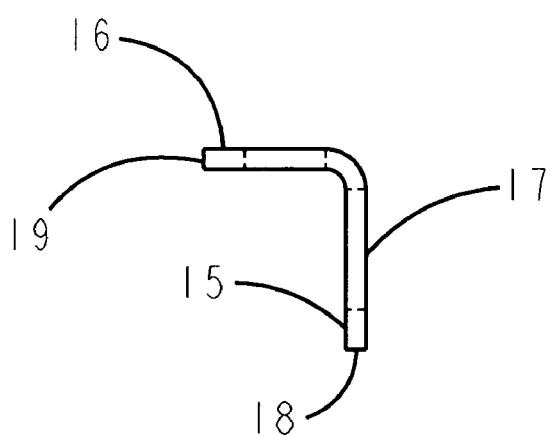
FIG. 2 is an end view of the arch bar of FIG. 1.
Figure 3:
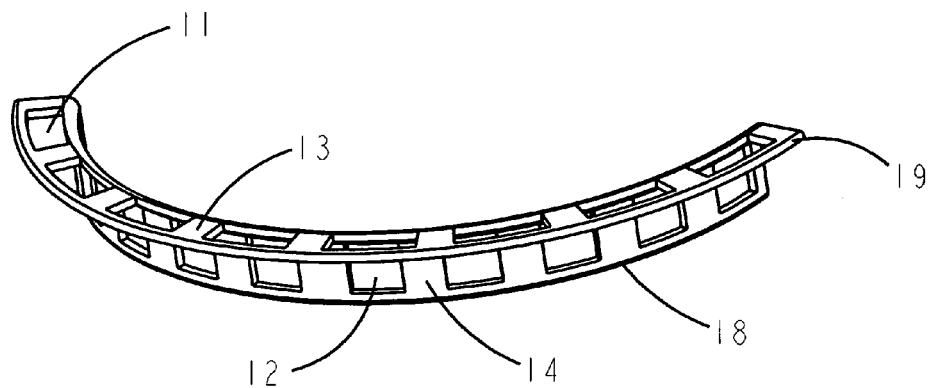
FIG. 3 is a perspective of the arch bar of this invention formed for application to a patient.

As shown in FIG. 2, the one piece arch bar has a splint portion 15 and a retainer portion 16 disposed at an angle of approximately 90 degrees. The splint portion 15 has a bone engaging surface 17 to be placed against the teeth or jaw. The splint portion is connected to the retainer portion along one margin and the lower margin is formed as a smooth rounded continuous surface 18. The retainer portion 16 is connected to the splint portion along one margin and forms a shelf with an outer margin that is a smooth rounded continuous surface 19. The smooth continuous surfaces 18 and 19 will be in intimate contact with the mucous tissues of the mouth. These surfaces reduce the irritation and trauma of the arch bar during use. As shown in FIG. 3, the arch bar will be manually formed to the final shape before it is applied to the injured jaw.

Figure 4:
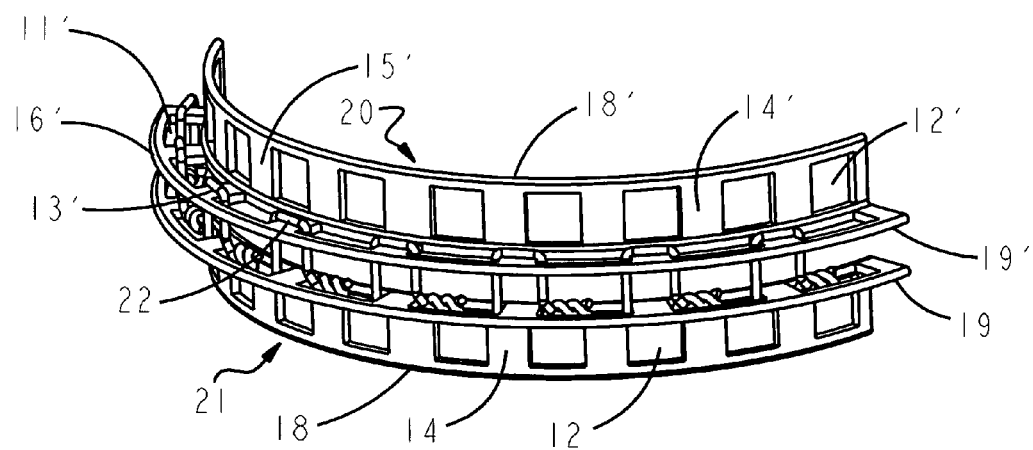
FIG. 4 is a perspective of an upper and lower arch bar with ligature wires disposed as applied to a patient.

In FIG. 4, two arch bars are shown as they would appear in use. As shown, the upper arch bar 20 and the lower arch bar 21 are not attached to the body. In use, the splint portion of each is connected to the teeth or bone by ligature wires (not shown) passing through the apertures 12, 12' and secured around the partitions 14, 14' similarly to the wire 22. Alternatively, the splint portions may be attached by adhesives applied on teeth engaging surface 17. To fix the patient's jaws together, the ligature wire 22 is threaded through the apertures 11, 11' in the retainer portions 16 and 16∝ and secured around the posts 13, 13'. In this manner, the soft tissue of the mouth is separated from the ligature wires by the shelf formed by the retainer portion of the arch bar. The splint portion 15' for the upper jar forms a mirror image of the splint portion 15 of the arch bar used for the lower jaw and illustrated in FIG. 2. The smooth continuous surface 18' and 19' will be in intimate contact with the mucous tissues of upper jaw, forming a mirror image of the smooth continuous surfaces 18 and 19 of the lower arch bar illustrated in FIG. 2.

It is to be understood that while I have illustrated and described certain forms of the invention, it is not to be limited to the specific forms of arrangement of parts here in described and shown. It will be apparent to those skilled in the art that various changes may be made without departing from the scope of the invention and the invention is not to be considered limited to what is shown in the drawings and described in the specification.

What is claimed is:

1. An improved arch bar having a splint portion for shielding ligature wires for protecting the soft tissue of the mouth from the ligature wires consisting of:

an upper arch bar and a lower arch bar being made of malleable material; said upper arch bar and said lower arch bar each formed into an arcuate shape having a convex side and a concave side; said upper arch bar and said lower arch bar each having a splint portion and a retainer portion; each said retainer portion disposed approximately normal to said splint portion on said convex side; each said splint portion having a teeth engageable surface on said concave side; a series of apertures through each said splint portion and each said retainer portion; each said aperture shaped as a window with four side walls with a side wall between adjacent apertures forming a post; each said splint portion and each said retainer portion terminating in a smooth continuous surface for engaging the inside of the mouth; wherein the arch bar is adapted to be secured to an individual by placing said splint portion against the teeth and wrapping ligature wires around at least two teeth, at least one post and passing through adjacent windows;

said splint portion of said upper arch bar adapted to be attached to the upper teeth; said splint portion of said lower arch bar adapted to be attached to the lower teeth; said apertures of each of said upper retainer portion and said lower retainer portion in approximate registry; said apertures in each said retainer portion separated by posts;

said improved arch bar further includes ligature wires that are threaded through one of each of said apertures in said upper retainer portion and said lower retainer portion and secured around one of each of the respective posts; and wherein said ligature wires are wrapped around adjacent posts for securement of said upper arch bar to said lower arch bar.

* * * * *